(12) United States Patent
Lu et al.

(10) Patent No.: US 9,636,890 B2
(45) Date of Patent: May 2, 2017

(54) LAMINATES WITH BONDED WEBS

(71) Applicant: The Procter & Gamble Company, Cincinnati, OH (US)

(72) Inventors: Jonathan Aaron Lu, Cincinnati, OH (US); Robert Haines Turner, Cincinnati, OH (US); Lisa Marie Reynolds, Hamilton Township, OH (US); Thomas Burkhart, Dahn (DE); Helmut Hartl, Branchweig (DE); Deying Kong, Vancouver, WA (US); David D. Newkirk, Greer, SC (US)

(73) Assignee: The Procter & Gamble Company, Cincinnati, OH (US)

( * ) Notice: Subject to any disclaimer, the term of this patent is extended or adjusted under 35 U.S.C. 154(b) by 313 days.

(21) Appl. No.: 14/263,062

(22) Filed: Apr. 28, 2014

(65) Prior Publication Data

US 2014/0234604 A1 Aug. 21, 2014

Related U.S. Application Data

(63) Continuation of application No. 13/005,237, filed on Jan. 12, 2011, now Pat. No. 8,728,051.

(Continued)

(51) Int. Cl.
*A61F 13/15* (2006.01)
*B32B 5/08* (2006.01)
(Continued)

(52) U.S. Cl.
CPC ............ *B32B 5/08* (2013.01); *A61F 13/5148* (2013.01); *D04H 3/14* (2013.01); *D04H 13/00* (2013.01); *A61F 13/53* (2013.01); *A61F 2013/51023* (2013.01); *A61F 2013/51026* (2013.01); *A61F 2013/51045* (2013.01); *A61F 2013/51052* (2013.01); *A61F 2013/51054* (2013.01); *A61F 2013/530226* (2013.01); *A61F 2013/530481* (2013.01); *B32B 2262/12* (2013.01); *B32B 2307/51* (2013.01); *B32B 2307/54* (2013.01); *B32B 2555/02* (2013.01); *Y10T 428/2481* (2015.01); *Y10T 442/64* (2015.04);

(Continued)

(58) Field of Classification Search
CPC .......... A61F 13/53; A61F 2013/530226; A61F 2013/530481; A61F 2013/51023; A61F 2013/51026; A61F 2013/51028; A61F 2013/51038; A61F 2013/51045; A61F 2013/51052; A61F 2013/51054
USPC ........ 604/370, 367, 372, 365, 378; 442/363, 442/394, 385; 428/196
See application file for complete search history.

(56) References Cited

U.S. PATENT DOCUMENTS

| | | |
|---|---|---|
| 5,108,827 A | 4/1992 | Gessner |
| 5,162,074 A | 11/1992 | Hills |

(Continued)

FOREIGN PATENT DOCUMENTS

| | | |
|---|---|---|
| WO | WO 96/16216 A1 | 5/1996 |
| WO | WO 2005/110719 A1 | 11/2005 |

OTHER PUBLICATIONS

PCT International Search Report, PCT-US2011-020960 date of mailing Apr. 7, 2011, 11 pages.

*Primary Examiner* — Jacqueline Stephens
(74) *Attorney, Agent, or Firm* — Sarah M. DeCristofaro; Charles R. Ware

(57) ABSTRACT

Laminates with a layer of bonded nonwoven material attached to a layer of film.

13 Claims, 5 Drawing Sheets

Related U.S. Application Data

(60) Provisional application No. 61/294,243, filed on Jan. 12, 2010.

(51) Int. Cl.

| | | |
|---|---|---|
| *A61F 13/514* | (2006.01) | |
| *D04H 3/14* | (2012.01) | |
| *D04H 13/00* | (2006.01) | |
| *A61F 13/53* | (2006.01) | |
| *A61F 13/51* | (2006.01) | |

(52) U.S. Cl.
CPC ........ *Y10T 442/641* (2015.04); *Y10T 442/642* (2015.04); *Y10T 442/674* (2015.04)

(56) References Cited

U.S. PATENT DOCUMENTS

| | | |
|---|---|---|
| 5,344,297 A | 9/1994 | Hills |
| 5,409,768 A * | 4/1995 | Dickenson ........ A61F 13/15626 442/389 |
| 5,466,410 A | 11/1995 | Hills |
| 5,529,665 A | 6/1996 | Kaun |
| 5,814,349 A | 9/1998 | Geus et al. |
| 5,869,172 A | 2/1999 | Caldwell |
| 6,207,602 B1 | 3/2001 | Gessner et al. |
| 6,288,144 B1 | 9/2001 | Roberts et al. |
| 6,352,700 B1 | 3/2002 | Luu et al. |
| 7,223,818 B2 | 5/2007 | Autran et al. |
| 7,422,712 B2 | 9/2008 | Delucia et al. |
| 2002/0119720 A1 | 8/2002 | Arora et al. |
| 2004/0033270 A1 | 2/2004 | Kropf et al. |
| 2004/0116018 A1 | 6/2004 | Fenwick et al. |
| 2005/0165173 A1 | 7/2005 | Autran et al. |
| 2008/0311814 A1 | 12/2008 | O'Sickey et al. |

\* cited by examiner

LAMINATES WITH BONDED WEBS

CROSS-REFERENCE TO RELATED APPLICATION

This application is a continuation of Ser. No. 13/005,237 filed Jan. 12, 2011 which claims priority to U.S. provisional application 61/294,243, filed Jan. 12, 2010, which is hereby incorporated by reference.

FIELD OF THE INVENTION

This application relates to laminates, in particular laminates with nonwovens and films.

BACKGROUND

Bonded webs, such as nonwoven fabrics are well known materials with wide application fields. Important applications encompass hygiene products and disposable articles, such as, for example, diapers. Many of these articles do not consist of a bonded web only, but include an elastomeric component to provide, for example, improved fit. This elastomeric component for instance is an elastic film. In a lamination process, the bonded web material is attached to this elastic film on one or on both sides of the film and provides the elastomeric component with a textile-like touch. Soft bonded webs are particularly suitable for such applications.

These laminates are generally produced on high-speed converting lines which apply tension in machine direction to the bonded webs. Applying tension to the bonded webs in machine direction will generally cause them to neck in, i.e. that their width is decreased. For obtaining optimal production, the bonded web is to completely cover the elastic film. However, during production, the tension applied to the bonded web varies. In such cases an ideal bonded web has a high dimensional stability, i.e. propensity to avoid neck-in in the cross-direction when under strain in the machine direction.

It is well known that a high dimensional stability can be obtained with bonded webs of high basis weight: the higher the basis weight of a bonded web, the higher is the force necessary to bring about neck-in. However, driven by the efforts to save raw materials and costs, low basis weights are desired instead of high basis weights. Thus, increasing the basis weight is prohibitive and other solutions that bring together low basis weights with high dimensional stability (under tension) are desired.

The technical challenge thus consists in bringing together and well balancing two contradicting properties: a sufficiently high cross-directional extensibility to allow mechanical activation, and a sufficiently high dimensional stability (low neck-in under machine direction tension) to make these materials processable on high speed converting lines.

SUMMARY OF THE INVENTION

It is one object of the present invention to cost-effectively provide bonded webs which are convertible on high-speed lines and which are mechanically activatable in, for example, the ring-roll processes, with high abrasion resistance.

The present invention relates to bonded webs and laminates that include such bonded webs. The continuous filaments forming the bonded webs have been thermally bonded to form the bonded webs. In various embodiments, these bonded webs have basis weights of less than or equal to 25 $g/m^2$, less than or equal to 22 $g/m^2$, less than or equal to 20 $g/m^2$, less than or equal to 18 $g/m^2$, or less, or any integer value between any of these values, or any range of values formed by any of the integer values.

Surprisingly the inventors found that bonded webs comprising continuous filaments comprising a first polymer material with a first melt temperature and a second polymer material with a second melt temperature which is higher than the first melt temperature fulfill the demanded properties if they are produced under a carefully selected and well balanced set of conditions. The bonded webs of the present invention are suitable candidates for high speed processing and mechanical activation. They have a high extensibility so that they are convertible on high-speed lines and survive mechanical activation in for instance the ring-roll process. Also they have a high dimensional stability for web handling in process converting operations. Also they have a low CD-tensile strength even in embodiments at low basis weights which helps enable survivability of mechanical activation. The bonded webs of the present invention comprise highly extensible multicomponent, preferably bicomponent, filaments or multiconstituent filaments or a mixture of said filaments and in an embodiment provide a high softness along with a high abrasion resistance. Abrasion resistance is particularly important to help reduce the level of fuzz for materials that are mechanically activated in more than one direction.

In various embodiments of the present disclosure, bonded webs have a neckdown modulus in the cross direction that is greater than or equal to 1000 N/m and less than or equal to 3000 N/m, greater than or equal to 1200 N/m and less than or equal to 3000 N/m, greater than or equal to 1400 N/m and less than or equal to 3000 N/m, greater than or equal to 1600 N/m and less than or equal to 3000 N/m, or greater than or equal to 2000 N/m and less than or equal to 3000 N/m, or any integer value between any of these values, or any range of values formed by any of the integer values.

Moreover, the bonded webs of the present invention can be mechanically activated due to their high extensibility in the cross direction that is greater than or equal to 80% and less than or equal to 300%, greater than or equal to 100% and less than or equal to 300%, greater than or equal to 120% and less than or equal to 300%, greater than or equal to 150% and less than or equal to 300%, or greater than or equal to 200% and less than or equal to 300%, (or any integer value between any of these values, or any range of values formed by any of the integer values) and due to their low tensile strength in the cross direction that is less than or equal to 4.0 N/cm, less than or equal to 3.5 N/cm, less than or equal to 3.0 N/cm, less than or equal to 2.5 N/cm, or less than or equal to 2.0 N/cm (or any value to the nearest 0.1 N/cm between any of these values, or any range of values formed by any of these values), Preferred bonded webs of the present invention are additionally characterized by an abrasion according to the Sutherland Ink Rub Test with a weight loss that is less than or equal to 0.25 $mg/cm^2$, less than or equal to 0.20 $mg/cm^2$, less than or equal to 0.15 $mg/cm^2$, less than or equal to 0.12 $mg/cm^2$, less than or equal to 0.10 $mg/cm^2$, less than or equal to 0.08 $mg/cm^2$ (or any value to the nearest 0.02 $mg/cm^2$ between any of these values, or any range of values formed by any of these values), From the bonded webs of this invention multilayered sheets or laminates may be prepared comprising at least one bonded web as defined above in contact with a layer of another sheet material. For example, a laminate can be formed with an elastic film and one or two or more than two layers of bonded webs attached to the film. Such laminates can also be incrementally stretched, in the cross direction, in the machine direction, or in both the cross direction and the machine direction, as described herein.

DETAILED DESCRIPTION OF THE INVENTION

Figure 1:
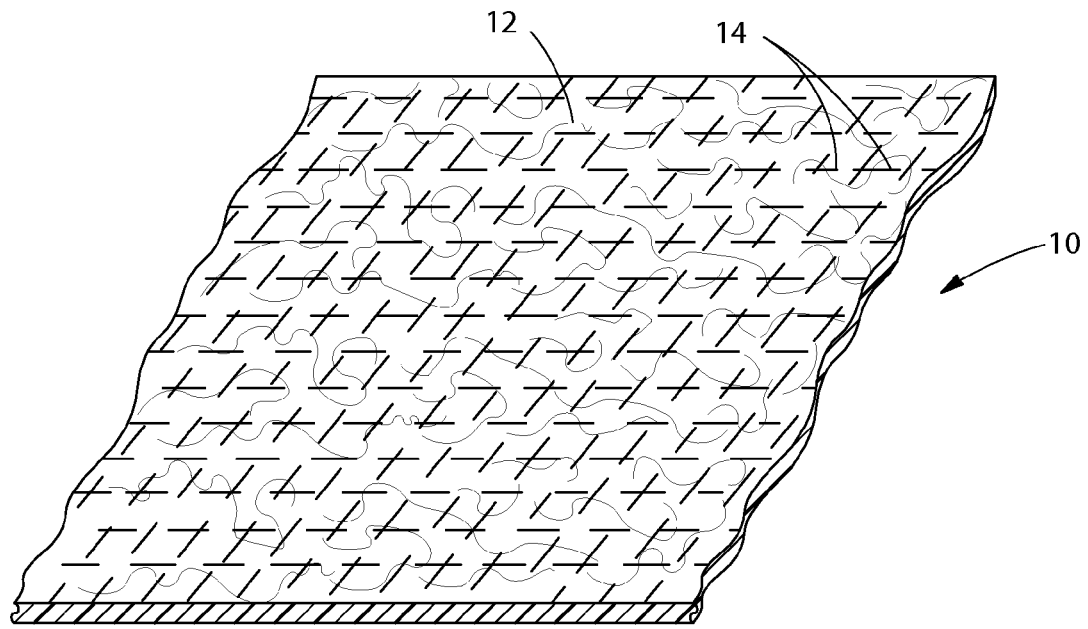
FIG. 1 is a perspective view of a spunbonded non-woven fabric formed of a plurality of multicomponent fibers.

FIG. 1 is a perspective view of a spunbonded non-woven fabric 10 formed of a plurality of continuous multicomponent fibers 12, at least some (e.g., all) of which are bonded with each other through a plurality of intermittent bonds 14.

Figure 2:
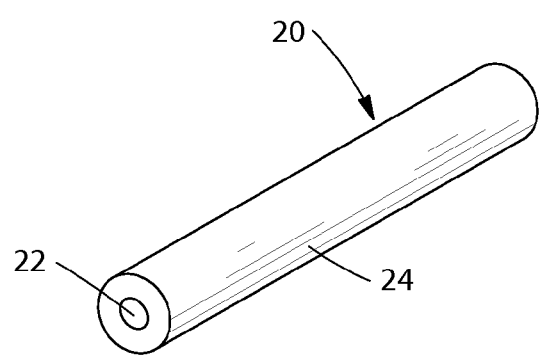
FIG. 2 is a perspective view of a multicomponent fiber.

FIG. 2 illustrates an exemplary multicomponent fiber 20 that includes a first component 22 and a second component 24.

Figure 3:
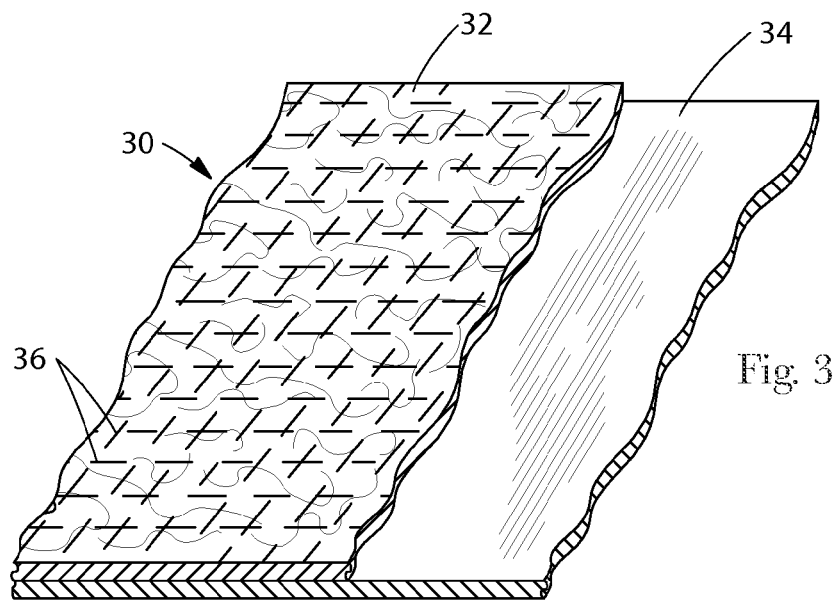
FIG. 3 is a perspective view of a non-woven laminate containing the fabric shown in FIG. 1, with the respective layers being exposed for clarity of illustration.

FIG. 3 is a perspective view of an exemplary laminate 30 with a nonwoven layer 32 having fibers 36 and a film.

Figure 4:
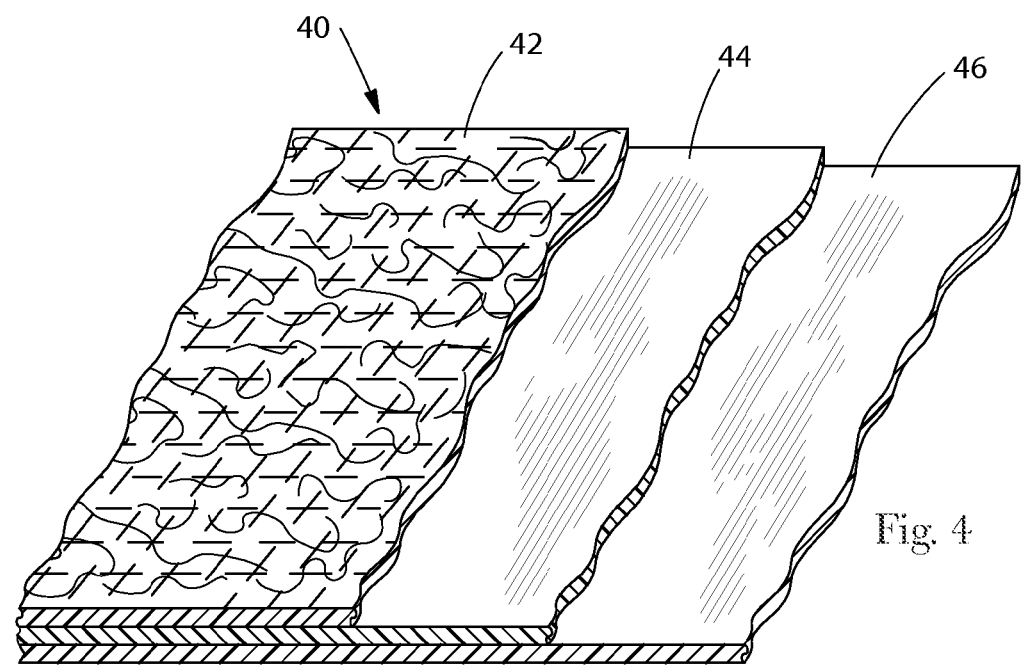
FIG. 4 is a perspective view of a trilayer non-woven laminate containing the fabric shown in FIG. 1.

FIG. 4 is a perspective view of an exemplary laminate 40 with a nonwoven layer 42 a film 44 and an additional layer 46 configured according to any embodiment of the present disclosure.

Materials made according to embodiments of the present disclosure can be incorporated into absorbent articles. It is contemplated that any embodiment of material disclosed herein can be used as part, or parts, or substantially all, or all of one or more of any element of an absorbent article.

An absorbent article can absorb liquid bodily exudates such as sweat, blood, urine, menses, etc. An absorbent article can be a product or a material. Examples of absorbent articles include products and/or materials for sanitary protection, hygienic use, and/or wound care.

Some absorbent articles are disposable. A disposable absorbent article is configured to be partly or wholly disposed of after a single use. A disposable absorbent article is configured such that the soiled article, or a soiled portion of the article, is not intended to be restored and reused (e.g., not intended to be laundered). Examples of disposable absorbent articles include wound care products, such as bandages and dressings, as well as feminine care products, such as pads and liners. Disposable absorbent articles can use embodiments of the present disclosure.

Some absorbent articles are wearable. A wearable absorbent article is configured to be worn on or around a body of a wearer. Wearable absorbent articles can also be disposable. Examples of disposable wearable absorbent articles include disposable diapers and disposable incontinence undergarments. A disposable wearable absorbent article can receive and contain bodily exudates while being worn by a wearer.

In some embodiments, a disposable wearable absorbent article can include a topsheet, an absorbent core, an outer cover, a waist opening, and leg openings. Disposable wearable absorbent articles can use embodiments of the present disclosure.

Figure 5:
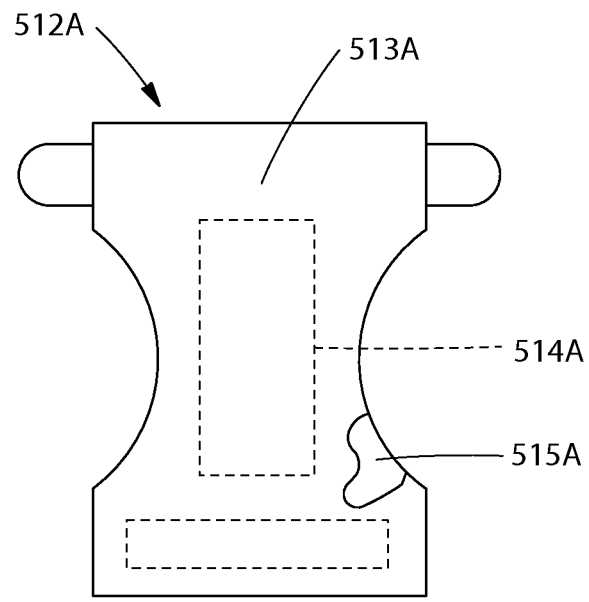
FIG. 5 is an inside plan view illustrating a front-fastenable wearable absorbent article.
Figure 6:
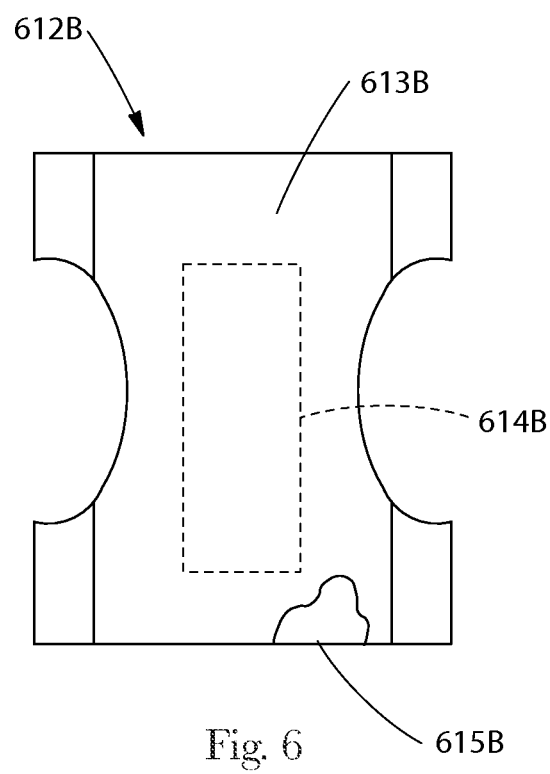
FIG. 6 is an inside plan view illustrating a pant-type wearable absorbent article.
Figure 7:
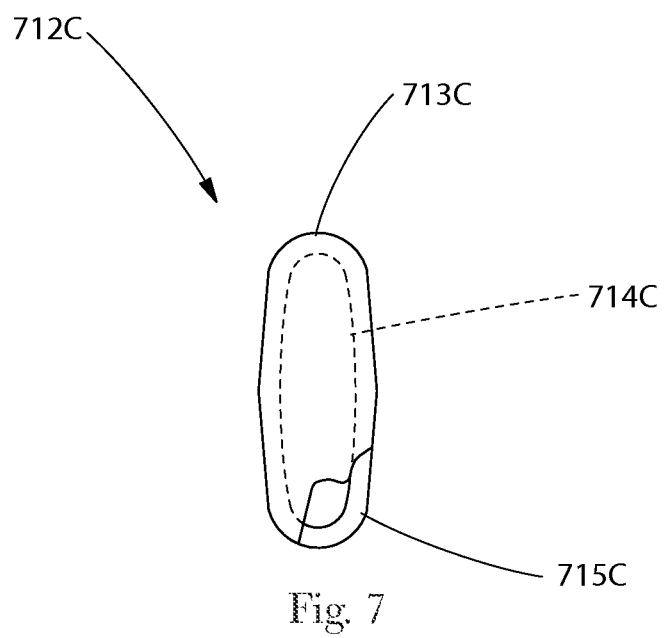
FIG. 7 is an inside plan view illustrating a feminine pad absorbent article.

FIGS. 5-7 illustrate various absorbent articles, with one or more elements made with materials according to embodiments of the present disclosure. For clarity, FIGS. 5-7 do not illustrate all details of the absorbent articles.

FIG. 5 is an inside plan view illustrating a front-fastenable disposable wearable absorbent article 512A. The present disclosure contemplates that, an absorbent article that is configured to be front-fastenable can also be configured to be rear fastenable or side-fastenable, as will be understood by one of ordinary skill in the art.

The front-fastenable wearable absorbent article 512A includes a wearer-facing external surface 513A, a garment-facing external surface 515A, and an absorbent material 514A. The absorbent material 514A is disposed between the wearer-facing external surface 513A and the garment-facing external surface 515A.

The wearer-facing external surface 513A is a layer of one or more materials that form at least a portion of an inside of the front-fastenable wearable absorbent article and faces a wearer when the absorbent article 512A is worn by the wearer. In FIG. 5, a portion of the wearer-facing external surface 513A is illustrated as broken-away, in order to show the garment-facing external surface 515A. A wearer-facing external surface is sometimes referred to as a topsheet. The wearer-facing external surface 513A is configured to be liquid permeable, such that bodily fluids received by the absorbent article 512A can pass through the wearer-facing external surface 513A to the absorbent material 514A. In various embodiments, a wearer-facing external surface can include a nonwoven material and/or other materials.

The absorbent material 514A is disposed subjacent to the wearer-facing external surface 513A and superjacent to the garment-facing external surface 515A, in at least a portion of the absorbent article 512A. In some embodiments, an absorbent material of an absorbent article is part of a structure referred to as an absorbent core. The absorbent material 514A is configured to be liquid absorbent, such that the absorbent material 514A can absorb bodily fluids received by the absorbent article 512A. In various embodiments, an absorbent material can include wood pulp, or super absorbent polymers (SAP), or another kind of absorbent material, or any combinations of any of these materials.

The garment-facing external surface 515A is a layer of one or more materials that form at least a portion of an outside of the front-fastenable wearable absorbent article and faces a wearer's garments when the absorbent article 512A is worn by the wearer. A garment-facing external surface is sometimes referred to as a backsheet. The garment-facing external surface 515A is configured to be liquid impermeable, such that bodily fluids received by the absorbent article 512A cannot pass through the garment-facing external surface 513A. In various embodiments, a garment-facing external surface 513A can include a non-woven fabric or laminate described herein. In other embodiments, a garment-facing external surface 513A can include a film and/or other materials.

The front-fastenable wearable absorbent article 512A also includes extensible side ears, configured to stretch around the sides of a wearer when the article 512A is worn. The extensible side ears also include a fastener, to fasten the back of the article to the front. Each of the extensible side ears can be formed of any of the embodiments of a laminate, as described herein. As a first example, a side ear can be formed of a nonwoven-film laminate that is incrementally stretched. As a second example, a side ear can be formed of a nonwoven-film-nonwoven laminate that is incrementally stretched. In either of these examples, additional materials can be added, and additional processing can be employed.

FIG. 6 is an inside plan view illustrating a pant-type disposable wearable absorbent article 612B. The present disclosure contemplates that, an absorbent article that is configured to be pant-type can be configured to be side-fastenable or without fasteners, as will be understood by one of ordinary skill in the art.

The pant-type wearable absorbent article 612B includes a wearer-facing external surface 613B, a garment-facing external surface 615B, and an absorbent material 614B, which are each generally configured in the same manner as the like-numbered element in the embodiment of FIG. 5.

The pant-type wearable absorbent article 612B also includes extensible side panels, configured to stretch around the sides of a wearer when the article 612B is worn. The extensible side panels may or may not include a fastener, to fasten the back of the article to the front. Each of the extensible side panels can be formed of any of the embodiments of a laminate, as described herein. As a first example, a side panel can be formed of a nonwoven-film laminate that is incrementally stretched. As a second example, a side panel can be formed of a nonwoven-film-nonwoven laminate that is incrementally stretched. In either of these examples, additional materials can be added, and additional processing can be employed.

FIG. 7 is an inside plan view illustrating a disposable feminine pad absorbent article 712C. The feminine pad absorbent article 712C includes a wearer-facing external surface 713C, a garment-facing external surface 715C, and an absorbent material 714C, which are each configured in a manner similar to the like-numbered element in the embodiments of FIGS. 5 and 6.

Figure 8:
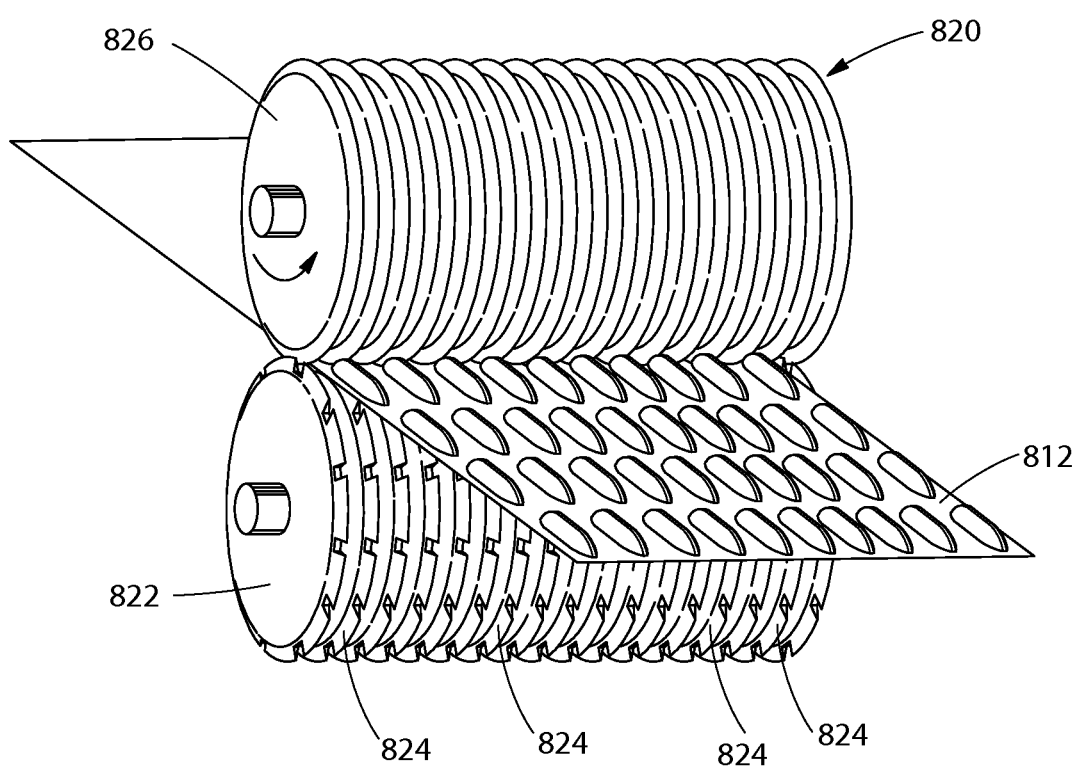
FIG. 8 illustrates an exemplary ring-rolling apparatus.

FIG. 8 illustrates an exemplary ring-rolling apparatus 820 used to incrementally stretch a web of nonwoven material 812 of the present disclosure. The apparatus 820 includes a patterned roll 822, including raised elements or teeth 824, and a non-patterned, grooved roll 826. The teeth 824 stretch the web of nonwoven material 812. It is contemplated that a web of nonwoven fabric or laminate of the present disclosure can also be incrementally stretched using variations of the ring-rolling apparatus 820 and/or one or more other kinds of stretching apparatus.

DEFINITIONS

The term "POLYMER" generally refers to homopolymers and copolymers, such as, for example, block, graft, random and alternating copolymers, as well as modifications thereof. Furthermore the term polymer shall include all possible molecular arrangements of the material. These arrangements include, but are not limited to isotactic, syndiotactic and random arrangements of the recurring units forming the polymer.

The term "POLYMER BLEND" refers to mixtures of at least two polymers with different physical and/or chemical properties. Thereby it is not important if these polymers are compatible or not.

The term "FILAMENT" refers to a thread of virtually unlimited length, whereas the term "FIBER" implies a definite length of the thread.

The term "MONOCOMPONENT FILAMENT" refers to a thread obtained by meltspinning one polymer melt stream through a spinning nozzle with one or multiple openings. The obtained filament has only one geometrically identifiable cross section that goes along the entire length of the filament. A monocomponent filament can be formed from one polymer. This embodiment is called a "HOMOFILAMENT". A monocomponent filament can also be formed from a polymer mixture. This embodiment is called a "MULTICONSTITUENT FILAMENT". The polymers forming the mixture can be compatible or incompatible with each other.

The term "MULTICOMPONENT FILAMENT" refers to a thread made from two or more separated polymer melt streams, which are combined in the spinning nozzle to form one single filament. This filament thus has a cross section that shows two or more identifiable areas extending continuously along the length of the filament. A preferred modification of multicomponent filaments are bicomponent filaments which are formed from two separated polymer melt streams. Most common are filaments with symmetric or asymmetric core-sheath, segmented pie, or side-by-side configuration. The polymers in the different sections usually differ in chemistry and/or physical properties.

The term "BONDED WEB" refers to a structure of individual fibers, filaments, or threads which are randomly laid. Bonded webs have been formed from many processes as, for example, meltblowing processes, spunbonding processes, and bonded carded processes, wherein some of the fibers are bonded by fiber-to-fiber fusion, by fiber entanglement, by use of adhesive or by thermal bonds such as point bonding. The basis weight of bonded webs is usually expressed in gram of material per square meter ($g/m^2$).

The term "SPUNBOND" refers to a bonded web containing substantially continuous filaments which are formed by extruding a molten thermoplastic material from a plurality of fine capillaries of a spinnerette. The diameter of the extruded filaments is then rapidly reduced by, for example, drawing them by a gas stream or by other mechanisms.

The term "CARDED BONDED WEB" refers to a bonded web consisting of fibers having a definite length, which have been laid to form a bonded web by means of a card. The fibers can be man-made and/or can be of natural origin.

The term "MACHINE DIRECTION" or "MD" refers to the dimension of a bonded web extending in the direction of movement of the bonded web during its production. MD is often referred to as the "length" of the bonded web.

The term "CROSS DIRECTION" or "CD" refers to the dimension of a bonded web extending perpendicular to the direction of movement during the production of said bonded web. CD is often referred to as the "width" of the bonded web.

The term "THERMAL POINT BONDING" refers to a process of consolidation of individual fibers into a formed web in which fusible polymer fibers or filaments in form of a bonded web pass between two heated rolls, e.g. a calender. Usually one of these rolls has an engraving giving pins with distinct geometry, area, and distribution. These pins press the bonded web towards the opposite second roll, heat the points of contact, and partially melt the filaments or fibers. These partially molten fibers are pressed together to form a bonding point of the same geometry as the pin. The mechanical properties of a bonded web strongly depend on the bond temperature. Bonding points may also be referred to as bonding regions herein.

The term "STANDARD CALENDERING TEMPERATURE" refers to that temperature that provides the bonded web with the highest tenacities. The standard calendering temperature is usually determined by preparing a variety of bonded webs which are distinguished by different calendering temperatures during thermal point bonding. The standard calendering temperature is that calendering temperature at which the spunbond nonwoven with the highest tenacity at break is formed under an otherwise fixed set of processing features, such as calendering pressure and speed. Calendering temperatures generally are monitored via the temperature of the calender oil.

The term "STICK POINT" refers to that temperature at which the bonded web starts to stick to the calender and at which processing becomes unreliable.

The term "EXTENSIBLE" or "EXTENSIBILITY" refers to the capability of a bonded web to stretch or extend in the direction of an applied force without structural failure. In contrast to elastic materials (see definition below) these terms do not necessarily imply recovery properties, and in general the extensible material keeps the once obtained dimension upon release of the applied force.

The term "ELASTOMERIC" or "ELASTIC" refers to the capability of a bonded web to stretch or extend into the direction of an applied force, and, upon release of the stretching force, return or contract to approximately the original dimension. An elastic material has at least a 75% recovery after a single extension of 10% of its original dimension.

The term "DIMENSIONAL STABILITY" refers to the property of a bonded web to resist a deformation perpendicular to the direction in which a force is applied. Such forces can occur, for example, during converting on high-speed diaper lines. This deformation perpendicular to the applied force is also called "NECK-IN". A characteristic key parameter to describe the dimensional stability is the NECK-DOWN MODULUS (in N/m). This term is obtained from a plot of bonded web width as a function of applied tension force. For smaller tensions this function is a straight line. The neckdown modulus is the negative slope of this line. For the purposes of this invention the neckdown modulus is determined from the bonded web-width/tension force diagram by fitting a line to the bonded web-width values obtained for tensile forces between 0 and 24 N/m at 2 N/m intervals.

The neckdown modulus represents the behaviour of a bonded web to neck-in under tension and is a characteristic parameter to describe dimensional stability. The higher the neckdown modulus the higher the dimensional stability.

The term "ELONGATION IN CROSS DIRECTION" refers to the elongation of the bonded web when extended in CD with maximum peak. The determination is performed in accordance to DIN EN 29073-3.

The term "TENSILE STRENGTH IN CROSS DIRECTION" refers to the tensile strength of the bonded web when extended in CD with maximum peak force. The determination is performed in accordance to DIN EN 29073-3.

The term "BOND AREA" refers to the portion of the area of the bonded web which contains bonded filaments. The bond area is determined in the non-stretched state of the bonded web and is the sum of the area provided by all bonding points of the bonded web. This term is expressed as a percentage of the total area of the bonded web.

The term "MULTILAYERED SHEET" refers to a composite of at least two layers of the same or different kind of sheet material. This can be, for example, a combination of a spunbond layer with a meltblown layer, a combination of two spunbond layers that differ in fiber geometry, polymer composition, or a combination of a spunbond layer with a film. The combination of a layer of bonded web with a layer of film is referred to as a "LAMINATE". These laminates result from a specific lamination process.

The term "MECHANICAL ACTIVATION" refers to a process of incremental stretching of a bonded web, a multilayered sheet, or a laminate, which, for example, comprises at least one extensible component and one elastomeric component. This can be, for example, a laminate of an extensible bonded web with an elastic film. During the incremental stretching the extensible component is permanently elongated. In case the extensible component is combined with an elastic component, the elastic component goes back to approximately its original position after release of the stretching force, while the extensible material keeps its then obtained extension. This gives the combination a softer hand.

The term "RING-ROLLING" refers to a specific variant of mechanical activation. This is an incremental stretching process which is applied to bonded webs, multilayered sheets, and laminates containing a nonwoven. Thereby the material is passed through intermeshing teethed rollers as described in US-A-2002/0119720.

Regarding bonded web-formation technology with the exception of consolidating the formed spunbond nonwovens by calendering the nonwovens of the present invention can be manufactured by conventional technology. Spinning technology is described, for example, in F. Fourné, Synthetische Fasern, chapters 4 and 5, pp. 231-596, Carl Hanser Verlag, München, 1995. Examples of spinning technology are Reicofil technology from Reifenhäuser Maschinenfabrik, Troisdorf, Germany, Hills technology from HILLS, Inc., W. Melbourne, Fla. 32904, USA, Neumag technology from NEUMAG GmbH, Neumünster, Germany or the S-Tex process. These processes are described by the manufacturers, and detailed information can be found on their corresponding homepages. In general, thermoplastic polymers are molten in an extrusion process and the melt is squeezed through nozzles to give a polymer strand. This polymer strand is cooled and stretched by a gas stream or, alternatively, by a mechanical means such as, for example, a galette, or by the combination of gas stream and mechanical means. The thus obtained fine filaments are collected in a random manner on a transporting means to form a bonded web.

In a preferred embodiment of the process of this invention the filaments are quenched with streams of air impinging from two sides upon the filaments after their formation.

In another preferred embodiment of the process of this invention the filaments are collected on a collecting means to form a non-consolidated web with no or only low fiber orientation. Preferred bonded webs are characterized by a ratio of MD tensile strength/CD tensile strength of less than 3, preferably of less than 2.5.

In still another preferred embodiment of the process of this invention the filaments are formed from spinning beams with a number of spinning holes of less than 7.500 per meter, preferably between 5.000 and 7.000 per meter. The diameter of the spinning holes is preferably at least 0.5 mm.

Preferably the bonded webs of the present invention are spunbonds.

The filaments that form the bonded webs of the present invention comprise a first polymer material with a first melt temperature and a second polymer material with a second melt temperature. The second melt temperature is higher than the first melt temperature. In general, the filaments are either multiconstituent filaments or multicomponent filaments or a mixture of these. Besides these filaments adjuvants conventionally used in bonded webs can be present.

These can be components present in the polymer strands forming the filaments, such as pigments, antistatic agents or fillers and/or components present at the surface of the filaments, such as lubricants or other processing aids. In addition small amounts of other filaments, for example homofilaments, can also be present. The amount of these adjuvants and/or other filaments in general is not more than 10 weight % of the bonded web.

Filaments with round geometry can be used, but other geometries, for example, triangular, might also be used. The multicomponent filaments can be of side-by-side-type or of core-sheath-type. Even multicomponent filaments of island-in-the-sea or segmented-pie-type are possible. Preferred in this invention are multicomponent filaments, very preferred bicomponent filaments of the core-sheath-type. Nevertheless, also mixtures of these fiber types can be used, if, for example, a multibeam spinning line is available.

The ratio to which extent the volumes of the core and of the sheath contribute to the whole filament is called the core-sheath-ratio. Preferred core/sheath ratios range from 95/5 to 5/95, very preferred from 85/15 to 50/50.

The filaments in the bonded webs of this invention generally are made from thermoplastic polymers or their blends. Preferred are polyolefins such as polypropylene or polyethylene, including their homopolymers as well as their copolymers. These polyolefins can be Ziegler-Natta- or metallocene-catalyzed polyolefins.

It is often sufficient to use these polyolefins without further modifying them by mixing or blending with other polymers, or by other modifications. For bicomponent filaments of the core-sheath-type, for example, it might be sufficient to have one single polymer in the core and another single polymer in the sheath. Specific examples are bicomponent filaments where the core consists of a metallocene- or Ziegler-Natta-polypropylene and the sheath consists of a polyethylene (for example of HDPE or LLDPE).

The use of polymer blends is also possible. In one embodiment the polymers are compatible with each other or even miscible. Such blends can consist of, for example, two polypropylenes that differ in molecular weight or in molecular weight distribution, or of a mixture between a polypropylene and a polyolefin copolymer. Such blends are described, for example, in U.S. Pat. No. 7,223,818 (US-A-2005/164,586) and U.S. Pat. No. 7,491,70 (US-A-2005/165,173). It should be understood that such blends are also possible for polyethylenes.

In another embodiment, the polymers blended together are at least partly miscible or even immiscible and form a dominant continuous phase and at least one dispersed phase. Examples of such mixtures are blends of polyethylene with polypropylene. These blends can also include a third component that is at least partially miscible with the two phases, for example, a copolymer of polypropylene with polyethylene. WO-A-96/16216, U.S. Pat. Nos. 5,108,827, and 6,207,602, for example, describe such mixtures.

A particularly suitable blend consists of isotactic polypropylene, present in an amount of about 65 to 80 percent by weight based upon the weight of the blend, of polyethylene, present in an amount from 1 to 5 percent by weight based upon the weight of the blend, and of a block or grafted polyolefin copolymer or terpolymer having at least a portion of the chain thereof miscible with the isotactic polypropylene, and wherein the block or grafted polyolefin or terpolymer is present in an amount from 15 to 30 percent by weight based upon the weight of the blend.

It should be understood that such blends not only can be spun as multiconstituent filaments, but can also be used in multicomponent filaments. Preferred are bicomponent filaments of the core-sheath-type that have a core-material selected from the group of polypropylenes or polyethylenes, mixtures of polypropylenes or mixtures of polyethylenes, polyethylene-polypropylene copolymers, mixtures of polypropylene with polyethylene or mixtures of polypropylene with polyethylene and polyethylene-polypropylene copolymers. The sheath-material is mainly selected from the group of polypropylene or polyethylene, but can also consist of the same combinations as the core. A very preferred combination is a bicomponent filament with polypropylene in the core and polyethylene in the sheath.

The bonded webs of this invention can consist of one bonded web layer only or can be used in multilayered sheets, for example a combination of a meltblown layer with at least one spunbond layer. Preferred is a single spunbond layer or a multilayered sheet comprising at least one spunbond layer. In an embodiment these bonded webs or multilayered sheets are laminated to an elastic film, or a net of elastic threads or strands by state of the art technology, and mechanically activated, for example, by ring rolling.

The basis weights of the bonded webs of this invention are in general less than or equal to 25 $g/m^2$, less than or equal to 22 $g/m^2$, less than or equal to 20 $g/m^2$, less than or equal to 18 $g/m^2$, or less. The bonded webs of this invention provide a high dimensional stability and a high extensibility to make them convertible on high-speed lines, and mechanically activatable in, for example, ring-roll processes.

Dimensional stability is an advantageous property for bonded webs to be converted on high-speed diaper lines for several reasons. There can occur, for example, sudden changes in bonded web tension caused by the machinery or by slow-down and subsequent acceleration processes that cause dimensional deformation in CD-direction. If the bonded web sensitively reacts to tension changes it will perceivably vary in bonded web width.

These bonded webs often will be laminated to an elastic film of a defined width. This film should be completely covered by the nonwoven. Tolerances range in the area of millimeters. If the bonded web width is reduced too much by tension, that is if the neck-in of the bonded web is too high, it will not exactly fit to the film anymore. This produces waste and stands opposite to the efforts to save raw materials and costs.

The dimensional stability of a bonded web can be determined by measuring its neck-down modulus. A method to do this is described in the section "Testing methods". This method records the loss of bonded web width at different and well defined bonded web tensions. The data allow the calculation of the neckdown modulus, which is the parameter to quantitatively describe the bonded web's inclination to neck-in under tension. A bonded web with a low neckdown modulus can more easily be deformed than a bonded web with a high neckdown modulus. Practical experience taught that neckdown moduli greater than or equal to 1000 N/m and less than or equal to 3000 N/m, greater than or equal to 1200 N/m and less than or equal to 3000 N/m, greater than or equal to 1400 N/m and less than or equal to 3000 N/m, greater than or equal to 1600 N/m and less than or equal to 3000 N/m, or greater than or equal to 2000 N/m and less than or equal to 3000 N/m allow a reliable processing. Several key parameters rule the neckdown modulus, such as, for example, basis weight, fiber polymer, fiber size, and bonding conditions, to name a few.

The bonded webs according to the present invention do not only have the demanded neckdown modulus, but also have a high extensibility. This property is very important as it allows mechanical after treatments, for example, by ring-roll processes, without damaging the nonwoven.

The extensibility of a bonded web usually can be determined together with its tensile strength on standard tensile testers, such as offered from Zwick/Roell (Ulm, Germany) or Instron Deutschland GmbH (Pfungstadt, Germany). Test methods are standard methods. For the purposes of this invention the stress-strain curves are determined according to DIN EN 29073-3.

Extensibility is ruled by parameters such as basis weight, fiber polymer, fiber size, bonding conditions, and process conditions, to name the most prominent.

Particularly fiber size and fiber polymer have an obvious impact on these mechanical properties. Bonded webs from polypropylene generally show extensibilities well below 80%, whereas bicomponent filaments of the core-sheath-type often show extensibility up to 150% and more. The extensibility also increases with increasing fiber titer, but this effect generally is less prominent than the material effect.

The following table compares the elongation of some standard bonded webs made from polypropylene and from polypropylene/polyethylene bicomponent filaments. As these standard bonded webs have these elongation, they also have the corresponding extensibility. It also illustrates the technical challenge: a high extensibility goes along with a low dimensional stability (expressed by a low neckdown modulus).

| Bonded web | CD-Elongation (%) | Neckdown modulus (N/m) |
|---|---|---|
| 18 g/m$^2$; polypropylene | 56 | 1200 |
|  | 40 | 1700 |
| 18 g/m$^2$; polypropylene/polyethylene bicomponent 50/50 | 195 | 425 |
|  | 179 | 716 |

Not only extensibility is important for mechanical after treatments. Another factor is the force necessary to achieve a certain degree of extension. This is expressed by the CD tensile strength. Background is that the energy input into the nonwoven during the activation process should not be too high. Otherwise the bonded web cannot take up the amount of energy and breaks. Experience leads to a desire for a tensile strength in CD of less than or equal to 4.0 N/cm, less than or equal to 3.5 N/cm, less than or equal to 3.0 N/cm, less than or equal to 2.5 N/cm, or less than or equal to 2.0 N/cm in addition to their high extensibility.

Objective of the present invention thus is to bring together two properties that mutually exclude each other: a high extensibility of the bonded web combined with a high dimensional stability.

The solution provided by this invention consists in the bonded web described above. This bonded web is prepared by using conventional bonded web-forming technology, preferably by using conventional spunbond technology but by using a special bonding process. This process results in a very well balancing of a sufficiently high bond area of the calender with a bonding temperature close to but still below the stick point of the bonded web. This is combined with an appropriate fiber size that still allows a high extensibility. In contrast to general expectations it has been surprisingly found that the extensibility of the bonded web does not decrease significantly under these well balanced conditions.

The bond area preferably covers between 16 and 35% of the total area of the bonded web, preferably between 20 and 30%.

The thermal point bonding of the bonded web is preferably performed by the action of one or more calenders. Different shapes of the single bonding points (or bonding regions) can be used at the calenders, such as oval or rhombic shape, but any other shape of the bonding region may also be used successfully. The single bonding points are arranged on the calender in such a way and amount to get a defined bonding pattern and a defined bonding area. Bonding patterns of regularly repeating bonding points can be used, for example bonding points arranged in the form of repeating hexagons, squares, triangles or lines. Alternatively randomly distributed bonding points can be used.

A thermal calendering process allows a very efficient and economic bonding of bonded webs made from thermoplastic polymers. A parameter of this technology is the temperature, which should be adjusted towards the fiber polymer. If the calender temperature is too high, the filaments will melt and stick to the rolls, bringing along a production stop and cleaning costs for the calender. If, on the other hand, temperature of the calender is too low, the filaments will not get bonded, and the bonded web looses dimensional stability, which makes further processing and converting impossible.

To avoid these difficulties, the bonding of the bonded web generally is done at a calender temperature that provides the bonded web with maximum strength and often also with maximum extensibility. However, the obtained maximum strength, particularly in CD direction, conflicts with the capability of the materials to be mechanically activated. The then necessary high force to bring about a certain extension increases the likeliness that the substrate will be destroyed during activation.

The bonded webs of this invention are not bonded at standard calender temperatures to provide them with maximum strength, but at calender temperatures between the stick point and the standard temperature that provides them with maximum strength. Due to the shape of a typical bonding curve (function of bonded web tensile breaking strength versus calendering temperature), the tensile strength decreases such that tensile values below 17.5 N/5 cm can be achieved.

However, also the extensibility is affected, which can make a careful adjustment of the titer necessary. It has been found that filaments with titers between 1 dtex and 3 dtex, very preferred between 2 and 2.8 dtex are particularly suitable for the bonded webs of the present invention. In various embodiments, filaments can range from 1.6 to 3.6 dtex, from 1.8 to 3.4 dtex, from 2.0 to 3.2 dtex, from 2.2 to 3.0 dtex, or from 2.4 to 2.8 dtex. Within these titer ranges, particularly bonded webs from core-sheath-type bicomponent filaments give the demanded low tensile strength in CD direction and still provide the bonded web with sufficient extensibility to allow undamaged activation.

Another characteristic of the bonded web of the present invention is their high abrasion resistance. This is particularly true for bicomponent filaments based on polypropylene core and polyethylene sheath.

The bonding conditions that provide the bonded webs with high tensile strength usually do not provide them with the abrasion resistance demanded for mechanical after treatments. Abrasion resistance depends on the quality of the bonding point, and depends on how well the fibers of the bonded web are welded together. This usually is no issue for filaments made from only one polymer, for example, polypropylene, but selecting the bond conditions is a parameter to consider if the fiber consists of two incompatible polymers as is the case in polypropylene/polyethylene bicomponent filaments whereby the polyethylene is used in the sheath It is clear that a high polyethylene content of the fiber then is very advantageous for the bonding strength.

However in relation to other aspects, a high polypropylene content is preferred. The polypropylene not only reduces the material costs, but it also helps improving dimensional stability of the whole bonded web without sacrificing extensibility. Thus, preferred core/sheath volume-ratios range between 85/15 to 50/50.

However, the bond temperatures usually used for pure polypropylene are well above the melting point of polyethylene and may even be close to the stick point of polyethylene. The use of such temperatures for these bicos, wherein the polyethylene is used in the sheath inevitably would cause sticking of the bonded web to the calender, and a roller wrap would follow. This is because the polyethylene in the sheath is the first material to be exposed to the heat of the calender (i.e. it experiences the highest temperatures, only conducting heat to the core material which has a higher melting point and sticking point) and is in direct contact with the calendar.

To achieve a high abrasion resistance for the bonded webs, the present invention combines a high bond area typical for the bonded webs of this invention with a high bond temperature. It has been found that bonding such bonded webs at calender temperatures close to the stick point of the bonded web are particularly effective. The skilled man will appreciate that the calendar temperatures are preferably chosen below the stick point. Very helpful is an additionally high bond area of the calender, which generally amounts between 18% and 25% of the total area of the bonded web. To achieve the necessary higher bond temperatures it may be of advantage to use calenders that show a lower adhesion to the softened or molten polymers, for example, to use calenders with rolls modified by a special surface treatment to result in anti-stick properties of the calendar surface, for example by covering the surface of one or more calender rolls with a sheet made of fluoropolymer, such as poly-tetrafluoroethylene. Utilization of higher bond temperatures allows measurement results for abrasion resistance, according to the Sutherland Ink Rub Test, of less than 0.25 mg/cm$^2$.

TESTING APPARATUS AND TESTING METHODS

Determination of Neckdown Modulus

Neckdown modulus can be determined in various methods, with as will be understood by one of ordinary skill in the art. That is to say, there is more than one measurement method that can lead to accurate and consistent results. The following presents one method for determining neckdown modulus in a bonded web of the present disclosure.

First, obtain the following supplies and test equipment: a calibrated linear scale that is at least 40 cm in length, common single-side adhesive tape (e.g. masking tape or duct tape) that is at least 50 mm wide, a clean, smooth, flat, non-sticky, and unobstructed horizontal testing surface (such as a large table-top) that is at least 400 mm wide and 2 m long, a calibrated tensile force gage with a capacity of at least 25 N (such as a Medio-Line 40025 available from Pesola AG, Baar, Switzerland), and a rigid dowel at least 0.5 mm long, with a section of an inelastic string tied to each end of the dowel.

Second, obtain and prepare the test sample. The test sample must be a web between 275-325 mm in width (cross-direction) and 1.8-2 m long (machine-direction). The test sample must lay flat under no tension for at least 30 minutes prior to this testing. The test should be performed at 25° C. with a relative humidity of about 75%.

Third, conduct the testing. Lay the prepared sample flat on the testing surface. Affix one MD end of the sample to the table using the tape. On the other (unaffixed) MD end of the sample, fold 5-10 cm of the sample over the dowel and tape that end to the web, so that a tensile force may be applied evenly across the width of the web by pulling on the dowel string in the machine direction.

Fourth, collect measurements. With the sample laying flat, and no pulling force applied to the dowel string, use the linear scale to measure the width of the sample at the middle of the web (e.g. 0.9-1 meters along its length). Record the linear distance as width at zero N of force. With the sample laying flat on the testing surface, attach the measuring hook of the force gage onto the middle of the dowel string, pull on the fixed end of the force gage, in the machine direction of the test sample, until the gage registers a specified force; hold at that displacement and while holding the test sample in tension at the specified force, use the linear scale to measure the width of the sample at the middle of the web. Record the linear distance as width at specified force. Collect width measurements at force values from 2-24 N, at increments of 2 N.

Fifth, calculate the neckdown modulus. Using the force and width data collected by the measurements, calculate the linear change in tension over the change in width, in units of N/m. This value is neckdown modulus.

Determination of the Titer

The fiber size is determined with a microscope having an internal ruler in either scale units or microns. The titer is then calculated with regard to the polymer density in either dtex (g/10000 m) or in denier ("den", g/9000 m).

Sutherland Ink Rub Test (Abrasion Resistance)

The abrasion resistance was measured by using the Sutherland Ink Rub test. The test was performed generally following ASTM method 5264 except that 320 grit sandpaper and a one pound weight were used. Specifically, after a surface of a fabric test sample was abraded by rubbing for 20 cycles at a rate of 42 cycles/minute, a fiber removal tape (a polymask protection tape sold by 3M as part number 3126) was held against the fabric test sample for 20 seconds under a weight of 2,200 grams. The fiber removal tape was weighted before and after application to the abraded surface. The change in weight was recorded to give the weight of fuzz removed from the abraded test sample. Three specimens of each fabric candidate were abraded to allow an average to be generated.

The Sutherland Ink Rub test used a sample size of 11.0 cm×4.0 cm and therefore had a 44 cm$^2$ area in contact with the sandpaper. The weight loss measured by the test was reported as mg/cm$^2$. A 27 g/m$^2$ HEC fabric sample (Fiberbonded web, Simpsonville, S.C.) was used as a control. The control sample (5 specimens) was abraded with each set of fabric candidates in order to obtain the correlation factor needed for the calculation of the Ink Rub Test result. The correlation factor was needed to account for differences in results due to lot to lot changes in the sandpaper. As specified in the ASTM test method, the final Ink Rub Result was calculated based on this correlation factor and the actual measured weight loss of the fabric.

Ring-Roll Tests

Ring-rolling tests were performed on pilot ring-roll equipment. The ring distance was 1.5 mm and the engagement depth was 2.0 mm. After ring-rolling the samples were visually characterized, whether bonding points were damaged or holes had occurred.

The bonded webs, multilayered sheet, incrementally stretched bonded webs and incrementally stretched multilayered sheet of this invention can be used after ring-rolling in hygiene products, such as personal care articles or in medical articles, preferably in diapers or in femcare articles, and especially preferred for a topsheet, backsheet, backear or side panel cover of a diaper.

The following examples will explain the invention without limiting it.

COMPARATIVE EXAMPLES

These spunbonded bicomponent fabrics were produced on a pilot scale Reicofil-3 type line similar to the machines currently offered for sale by the Reifenhauser Company. Machinenfabrik in Troisdorf, Germany (see, e.g., U.S. Pat. Nos. 5,162,074; 5,344,297; 5,466,410; and 5,814,349). The bicomponent fabrics were made using Dow 6834 HDPE (17 MI, density: 0.950) as the sheath polymer and Basell's Moplen HP462R (25 MFR) as the core polymer. Specifically, the spunbonded bicomponent fabric was produced by melting the sheath and core polymers in two different extruders, conveying the molten polymers to a spin bank or spin beam assembly (which included a spinneret plate and a distribution plate) connected to the extruders for separately receiving the molten sheath and core polymers, combining the polymers at the spinneret orifices to form a curtain of multicomponent fibers, quenching the fibers with cool air as they exited as a full width curtain of fibers, attenuating the fibers in the curtain, depositing the curtain (or multiple curtains depending on the number of spin beams) of attenuated fibers via a filament depositing unit (a diffuser) on a moving wire or moving conveyor belt, and then bonding the resulting bonded web of fibers to yield a non-woven fabric.

To make the fabrics, special attention was given to bonding the bonded web of spunbonded fibers. An embossed calender pattern was used, the calender temperature and fabric speed were carefully selected. Calender oil temperature used was "standard"; that is the temperature which results in the highest tensile strength of the fabric. While the calender temperature was not directly measured, the hot oil temperature circulating within the embossing and smooth rolls of the calender were significantly higher than the melting temperature of the polyethylene sheath polymer.

Comparative Example C1

Standard Polypropylene Spunbond

On a conventional spunbond RF3 line (Reifenhä user, Troisdorf, Germany), a 18 g/m$^2$ polypropylene spunbond was prepared. The polypropylene had a meltflow index (MFI) of 25 g/10 min (ISO 1133; 230° C., 2.16 kg). The throughput was set to 200 kg/h*m, and the belt speed was 169 m/min. The oil temperature of the calender was set to 150° C. The resulting nonwoven had the mechanical properties (according DIN 53857) as listed in the table at the end of the experimental part.

Comparative Example C2

Standard Spunbond Made from Bicomponent Filaments

The preparation of this spunbond was as described for Example C1 with the exception that polypropylene/polyethylene bicomponent filaments were formed with a volume ratio of 70/30. Typical bonded web properties are listed in the table at the end of the experimental part.

Examples According to the Invention

Examples 1-3

On a spunbond line with bicomponent capability, different spunbonds were prepared. The filaments prepared were of core/sheath type with polypropylene ("PP") core, polyethylene ("PE") sheath and with different core/sheath ratios. The PP had a meltflow index (MFI) of 25 g/10 min (ISO 1133; 230° C.; 2.16 kg) and the PE had a meltflow index of 17 g/10 min (ISO 1133; 190° C.; 2.16 kg). The line settings were adjusted such that the filaments had the desired average titer. Bonding of the spunbond nonwovens occurred with a standard calender and with different bonding areas. The bonding temperature was set above the standard bonding temperature. Details of the manufacture of the spunbond nonwovens and of their properties are given in the following table.

| Material | Fmax (CD) N/cm | Elongation in CD @ Fmax % | Titer dtex | Ink Rub Test Mg/cm2 | Neckdown Modulus N/m | Calender Bond Area % | Calender Oil Temperature |
|---|---|---|---|---|---|---|---|
| Example C1 20 g/m$^2$ PP spunbond | 5.2 | 64 | 2.4 | 0.150 | 1677 | 19 | standard |
| Example C2 22 g/m$^2$ PP/PE bicomponent 70/30 | 2.4 | 200 | 2.5 | 0.326 | 730 | 16 | standard |
| Examples of the Invention | | | | | | | |
| Example 1 21 g/m$^2$ PP/PE bicomponent 50/50 | 3.0 | 171 | 3.0 | 0.242 | 1591 | 34 | standard + 10° C. |

-continued

| | Fmax (CD) N/cm | Elongation in CD @ Fmax % | Titer dtex | Ink Rub Test Mg/cm2 | Neekdown Modulus N/m | Calender Bond Area % | Calender Oil Temperature |
|---|---|---|---|---|---|---|---|
| Example 2 22 g/m² PP/PE bicomponent 70/30 | 2.8 | 139 | 2.7 | 0.200 | 1641 | 18 | standard + 15° C. |
| Example 3 22 g/m² PP/PE bicomponent 70/30 | 2.4 | 88 | 2.5 | 0.080 | 1571 | 25 | standard + 25° C. |

Calender oil temperature: "standard" is that temperature which gives the highest tensile strength of the fabric.

In Example C1, pure PP spunbond fails in elongation and Fmax, which illustrates that a high neckdown modulus is linked with a low extensibility. In Example C2, the PP/PE bicomponent fails in neckdown modulus and abrasion resistance, which illustrates that a high extensibility is linked with a low neckdown modulus. Example 1 shows the benefits of an increased calender area and a slightly increased bond temperature, which results in improved abrasion resistance and clearly increased neckdown modulus compared to example C2. Example 2, when compared to example C2, shows the benefits of a clearly higher bond temperature: abrasion resistance and neckdown modulus drastically improve. Example 3 shows clearly the benefits of high bond area and high bond temperature (here close to the stick point), which results in a high neckdown modulus.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm.

All documents cited in the Detailed Description of the invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and the scope of the invention. It is therefore intended to cover in the appended claims all such changes and modifications that are within the scope of this invention.

What is claimed is:

1. A laminate comprising a layer of nonwoven material attached to a layer of film, wherein:
   the layer of nonwoven material comprises filaments of a first polymer and a second polymer;
   the first polymer has a first melt temperature, and the second polymer has a second melt temperature, wherein the second melt temperature is higher than the first melt temperature, and wherein the first polymer and the second polymer form a multicomponent filament wherein in cross section two distinct identifiable areas extending continuously along the length of the filament are present;
   the layer of nonwoven material is thermally bonded;
   the layer of nonwoven material has a machine direction and a cross direction;
   the layer of nonwoven material has:
   a neckdown modulus in the cross direction that is greater than or equal to 1000 N/m and less than or equal to 3000 N/m;
   a tensile strength in the cross direction that is less than or equal to 4 N/cm; and
   an extensibility in the cross direction that is greater than or equal to 80% and less than or equal to 300%.

2. The laminate of claim 1, wherein the basis weight is less than or equal to 25 gsm.

3. The laminate of claim 1, wherein the basis weight is less than or equal to 22 gsm.

4. The laminate of claim 1, wherein the basis weight is less than or equal to 16 gsm.

5. A laminate comprising a layer of nonwoven material attached to a layer of film, wherein:
   the layer of nonwoven material comprises filaments of a first polymer and a second polymer;
   the first polymer has a first melt temperature, and the second polymer has a second melt temperature, wherein the second melt temperature is higher than the first melt temperature, and wherein the first polymer and the second polymer form a multicomponent filament wherein in cross section two distinct identifiable areas extending continuously along the length of the filament are present;
   the layer of nonwoven material is thermally bonded;
   the layer of nonwoven material has a machine direction and a cross direction;
   the layer of nonwoven material has:
   a neckdown modulus in the cross direction that is greater than or equal to 1000 N/m;
   a tensile strength in the cross direction that is less than or equal to 4 N/cm; and
   an extensibility in the cross direction that is greater than or equal to 80% and less than or equal to 300%.

6. The laminate of claim 5, wherein the basis weight is less than or equal to 25 gsm.

7. The laminate of claim 5, wherein the basis weight is less than or equal to 18 gsm.

8. The laminate of claim 5, wherein the neckdown modulus in the cross direction is greater than or equal to 1200 N/m.

9. The laminate of claim 5, wherein the neckdown modulus in the cross direction is greater than or equal to 2000 N/m.

10. The laminate of claim 5, wherein the neckdown modulus is less than or equal to 3000 N/m.

11. The laminate of claim 5, wherein the tensile strength in the cross direction is less than or equal to 3.0 N/cm.

12. The laminate of claim 5, wherein the extensibility in the cross direction is greater than or equal to 100%.

13. The laminate of claim 5, wherein the extensibility in the cross direction is greater than or equal to 150%.

* * * * *